United States Patent
Pinguet et al.

(10) Patent No.: US 8,606,531 B2
(45) Date of Patent: Dec. 10, 2013

(54) SYSTEM AND METHOD FOR SPOT CHECK ANALYSIS OR SPOT SAMPLING OF A MULTIPHASE MIXTURE FLOWING IN A PIPELINE

(75) Inventors: Bruno Pinguet, Caracas (VE); Cheng-gang Xie, Sawston (GB); Paul Guieze, Fontenailles (FR); Graham Birkett, Houston, TX (US)

(73) Assignee: Schlumberger Technology Corporation, Houston, TX (US)

( * ) Notice: Subject to any disclaimer, the term of this patent is extended or adjusted under 35 U.S.C. 154(b) by 371 days.

(21) Appl. No.: 12/530,857

(22) PCT Filed: Mar. 19, 2008

(86) PCT No.: PCT/GB2008/000969
§ 371 (c)(1),
(2), (4) Date: Jan. 27, 2010

(87) PCT Pub. No.: WO2008/117024
PCT Pub. Date: Oct. 2, 2008

(65) Prior Publication Data
US 2010/0145634 A1    Jun. 10, 2010

(30) Foreign Application Priority Data

Mar. 27, 2007    (GB) .................................. 0705807.6

(51) Int. Cl.
*G01N 31/00*    (2006.01)
(52) U.S. Cl.
USPC .................. 702/24; 702/45; 702/47; 702/50; 702/54; 73/863.21
(58) Field of Classification Search
USPC .............................................. 702/45, 24, 50
See application file for complete search history.

(56) References Cited

U.S. PATENT DOCUMENTS 3,840,051 A    10/1974    Akashi et al.
4,060,001 A    11/1977    Archerd
(Continued)

FOREIGN PATENT DOCUMENTS

EP    0561557 A1    9/1993
EP    0690292 A2    1/1996
(Continued)

OTHER PUBLICATIONS

Fish, David J., "Isokinetic Crude Oil Sampling", Apr. 1992, Pipe Line Industry, pp. 1-8.*
(Continued)

*Primary Examiner* — Mischita Henson

(57) ABSTRACT

This disclosure relates in general to systems and methods for spot checking flow properties of a multiphase mixture containing one or more hydrocarbons flowing through a pipeline or the like. More specifically, but not by way of limitation, embodiments of the present invention provide systems and methods for creating slug-type flows of isokinetically obtained samples of the multiphase mixture flow. By spot checking the slug-type flow of an isokinetically obtained sample of the multiphase flow, embodiments of the present invention may provide for determining flow properties of gas, oil/condensate and/or water components of the multiphase flow. In certain aspects of the present invention, an active sampling device may be used to enrich one of the phases of the slug-type flow of the sampled multiphase mixture and/or take a representative sample of one of the phases of the slug-type flow of the sampled multiphase mixture.

17 Claims, 8 Drawing Sheets

(56) References Cited

U.S. PATENT DOCUMENTS

| | | | |
|---|---|---|---|
| 4,167,117 A | 9/1979 | Stokley et al. | |
| 4,301,679 A | 11/1981 | Boyle et al. | |
| 4,429,581 A | 2/1984 | Furmaga | |
| 4,442,720 A * | 4/1984 | Apley et al. | 73/863.31 |
| 4,510,060 A | 4/1985 | Stewart et al. | |
| 4,522,218 A | 6/1985 | Konak | |
| 4,566,342 A | 1/1986 | Kurz | |
| 4,574,643 A | 3/1986 | Scott et al. | |
| 4,776,210 A | 10/1988 | Baillie et al. | |
| 4,881,412 A | 11/1989 | Northedge | |
| 4,891,969 A | 1/1990 | Wayland et al. | |
| 5,099,697 A * | 3/1992 | Agar | 73/861.04 |
| 5,309,946 A | 5/1994 | Ligneul | |
| 5,337,595 A | 8/1994 | Lewis | |
| 5,363,696 A * | 11/1994 | Cardellini et al. | 73/61.44 |
| 5,535,632 A | 7/1996 | Kolpak | |
| 5,600,073 A * | 2/1997 | Hill | 73/861.04 |
| 5,654,502 A | 8/1997 | Dutton | |
| 5,762,107 A | 6/1998 | Laws | |
| 5,811,696 A | 9/1998 | Jobson | |
| 5,861,561 A | 1/1999 | Van Cleve et al. | |
| 5,894,080 A | 4/1999 | Dybdahl | |
| 6,041,668 A | 3/2000 | Guieze et al. | |
| 6,062,092 A | 5/2000 | Weaver | |
| 6,128,962 A | 10/2000 | Marrelli et al. | |
| 6,343,516 B1 * | 2/2002 | Marrelli | 73/861.04 |
| 6,546,809 B1 | 4/2003 | Andreussi | |
| 7,717,000 B2 | 5/2010 | Xie et al. | |
| 7,942,065 B2 | 5/2011 | Xie | |
| 2005/0016292 A1 * | 1/2005 | Dutton et al. | 73/861.03 |
| 2006/0236781 A1 * | 10/2006 | Ohmi et al. | 73/861.52 |
| 2008/0307860 A1 | 12/2008 | Guieze et al. | |

FOREIGN PATENT DOCUMENTS

| | | |
|---|---|---|
| EP | 0690292 A3 | 10/1997 |
| EP | 0764236 B1 | 8/2001 |
| GB | 2041035 A | 9/1980 |
| GB | 2272766 A | 5/1994 |
| GB | 2275990 A | 9/1994 |
| GB | 2277990 A | 11/1994 |
| GB | 2299167 A | 9/1996 |
| GB | 2301297 A | 12/1996 |
| GB | 2311606 B | 4/1998 |
| GB | 2333372 A | 7/1999 |
| GB | 2406386 A | 3/2005 |
| GB | 2432425 A | 5/2007 |
| GB | 2431010 C | 5/2008 |
| WO | 9108444 A1 | 6/1991 |
| WO | 9522400 A1 | 8/1995 |
| WO | 9812532 A1 | 3/1998 |
| WO | 9812533 A1 | 3/1998 |
| WO | 9833051 A1 | 7/1998 |
| WO | 0047870 A1 | 8/2000 |
| WO | 0049370 A1 | 8/2000 |
| WO | 0177489 A1 | 10/2001 |
| WO | 0220944 A1 | 3/2002 |
| WO | 2005031311 A1 | 4/2005 |
| WO | 2006005600 A1 | 1/2006 |
| WO | 2006037565 A1 | 4/2006 |
| WO | 2007060386 A1 | 5/2007 |

OTHER PUBLICATIONS

Dong, F., Xu, Y., Hua, L. and Wang, H., "Two Methods for Measurement of Gas-Liquid Flows in Vertical Upward Pipe Using Dual-Plane ERT System", Oct. 5, 2006, IEEE Transactions on Instrument and Measurement, vol. 55, pp. 1576-1586.*

Atkinson et al: "High-accuracy wet-gas multiphase well testing and production metering", SPE Annual Technical Conference and Exhibition, Houston, Texas, Sep. 26-29, 2004, SPE 90992.

Buurman et al: "Representative crude oil sampling during transfer operations", Petroleum Review, vol. 38, No. 454, 1984, pp. 47-49.

Dybdahl et al: "A systematic approach to sampling during well testing", SPE Latin American and Caribbean Petroleum Engineering Conference, Buenos Aires, Argentina, Mar. 25-28, 2001, SPE 69427.

Expro: "Fluids sampling and analysis", Expro Group, product information website: http://exprogroup.com/wp-content/uploads/EXP_FluidAnalysis_A4.pdf, Jan. 2, 2012.

Expro: "Fluids sampling and analysis. Introduction to Iso-Split sampling of gas/condensate and volatile oil reservoirs", Expro Group, product information website: http://exprogroup.com/downloads/Introduction%20to%20Iso-Split%20sampling%20of%20gas...pdf, Jan. 6, 2012.

Expro: "Fluids sampling and analysis. Iso-Split separators sampling", Expro Group, product information, website: http://exprogroup.com/downloads/Iso-split%20separators%20Sampling.pdf, Jan. 6, 2012.

Expro: "Fluids sampling and analysis". IsoSplit wellhead sampling, Expro Group, product information, website: http://exprogroup.com/downloads/Iso-Split%20wellhead%20sampling.pdf, Jan. 6, 2012.

Jayawardane et al: "PVT sampling with multiphase flowmeters—theoretical justifications and field limitations", SPE Annual Technical Conference and Exhibition, San Antonio, Texas, Sep. 29-Oct. 2, 2002, SPE 77405.

Konopczynski et al: "Large-scale application of wet-gas metering at the Oman Upstream LNG Project", 2000 SPE Annual Technical Conference and Exhibition, Dallas, Texas, Oct. 1-4, 2000, SPE 63119.

Kool et al: "Testing of gas condensate reservoirs—sampling, test design and analysis", SPE Asia Pacific Oil and Gas Conference, Jakarta, Indonesia, Apr. 17-19, 2001, SPE 68668.

Nakazatomi et al: "Effect of pressure on entrainment flow rate in vertical upwards gas-liquid annular two-phase flow. Part I: experimental results for system pressures from 0.3 MPa to 20 MPa", Heat Transfer—Japanese Research, vol. 25, No. 5, 1996, pp. 267-280.

Petrotech International: "IsoSplit: Wellhead and test separator sampling", product information, copyright 1999, reference printed on Sep. 24, 2003 from website: http://www.petronett.com/isosplit.htm (link no longer available).

Schraub: "Isokinetic probe and other two-phase sampling devices: A survey", Symposium on two-phase flow instrumentation, National Heat Transfer Conference, Minneapolis 1969, pp. 47-57.

Theuveny et al: "Multiphase flowmeter application for well and fiscal allocation", SPE Western Regional/AAPG Pacific Section Joint Meeting, Anchorage, Alaska, May 20-22, 2002, SPE 76766.

* cited by examiner

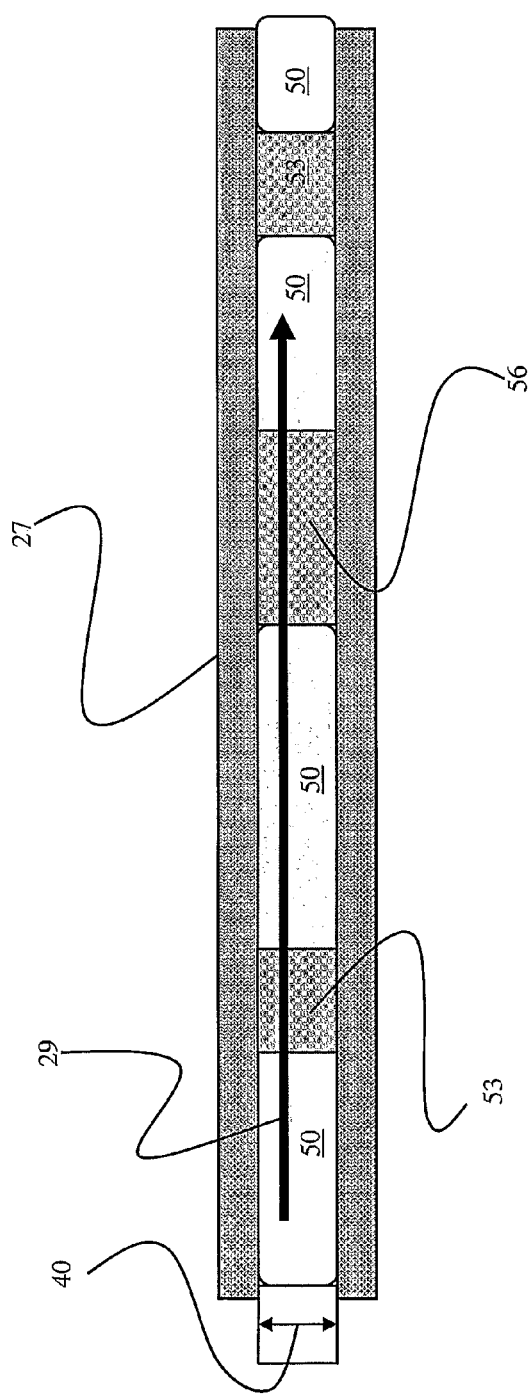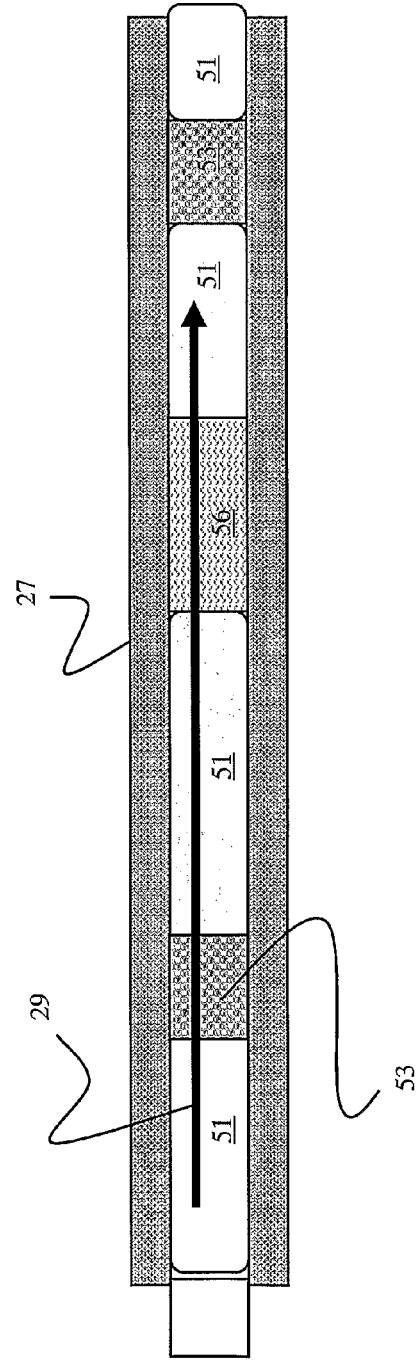
Fig. 2A
Fig. 2B

SYSTEM AND METHOD FOR SPOT CHECK ANALYSIS OR SPOT SAMPLING OF A MULTIPHASE MIXTURE FLOWING IN A PIPELINE

BACKGROUND OF THE INVENTION

This disclosure relates in general to a method and system for analyzing a multiphase mixture flowing in a pipeline. More specifically, but not by way of limitation, embodiments of the present invention provide for withdrawing a sample of the multiphase mixture under isokinetic conditions and flowing the withdrawn sample as a slug-type flow or pseudo slug-type flow, which slug-type flow provides that the phases of the multiphase sample are mostly separated between one essentially dominant (or close to continuous) liquid phase and another essentially dominant gas phase, through one or more measuring, detection, sampling and/or sensing devices. In such embodiments, from the measurements, detection, sampling and/or sensing of one or more of the separated phases in the slug-type flow, flow properties of the multiphase mixture and properties of the phases of the multiphase mixture may be processed. For purposes of this specification, but not by way of limitation, the term phase may be used to describe a gas phase, a liquid phase, a water phase or an oil phase of a multiphase mixture.

In the hydrocarbon industry, it is desirable during the production and/or transport of oil and gas to carry out measurements to determine the properties of a multiphase mixture flowing in a hydrocarbon pipeline where the multiphase flow may consist of a combination of oil, water, gas and/or the like. With regard to the liquid phase of the multiphase mixture, measurement of the properties of the oil and/or water, including among other things the amount of the oil and/or water in a hydrocarbon transporting pipeline is often highly desirable so as to control and regulate hydrocarbon production. For example, it may be important to measure oil being produced by not only an oilfield, but also individual oil wells associated with the oilfield. Measurements may be necessary/desirable in order to determine the water and/or the gas content of the flow being produced from individual oil wells—for production analysis, etc—and/or to allocate production amounts to individual rights owners.

The early detection of water is an important measurement for subsea gas condensate wells where inhibitors may be added to prevent the formation of scale and hydrates in the pipeline downstream of the well head. In such cases, expensive inhibitors may be pumped into the pipeline from the start of hydrocarbon production, the quantity of fluid being determined from reservoir models. To manage the use of the inhibitors, the detection and quantification of the water can result in significant cost savings. Furthermore, in aging oil wells where the gas-volume fraction (GVF) and/or water-cut can be very high (e.g., GVF>95% and/or water-cut>95%), the quantity of oil in the flow line determines the economics of the well.

It is, however, in general, very difficult to obtain measurements when the oil and/or water are flowing simultaneously with gaseous components through the pipeline. The problems associated with taking measurements arise, from among other things, the distribution of the different phases in the pipe—the phases may form different arrangements temporally and spatially—both axially and radially in the pipe. These different arrangements of the multiple phases may create, among other things, nonlinear responses—with the measuring system.

Flow of the multiphase fluid in the pipe may consist, among other flow designations, of a continuous phase—normally, liquid flow—or a discontinuous phase—normally, gas flow. In the continuous phase, the flow may be a continuous oil flow and the flowing oil may contain water droplets. Such flow, being primarily made up of a hydrocarbon substance, may, in general, be marked by low electrical conductance characteristics. In the alternative, the flow may be a continuous water flow with oil droplets distributed in the continuously flowing water. In such situations, the water, which may also have varying degrees of salinity, may provide that the flowing mixture has electrically conductive characteristics that change with time due to water injection or breakthrough, especially in contrast to the oil continuous situation.

With regard to the gaseous components of the multiphase fluid, the gaseous components may be distributed in large volumes or pockets in the multiphase fluid as gas churns or slugs, or may be distributed as small bubbles in the liquid phase, often referred to as bubble flow. Furthermore, under high pressure, such as found downhole, gas in the multiphase fluid may be dissolved in the oil phase. When there are large volumes of gas in the pipeline the gas may govern the multiphase fluid flow and cause the oil and water phase to be pushed back to the pipe wall. In this case, often referred to as annular flow, the oil/water fluid mixture may move at a low velocity along the pipe wall. Additionally annular-mist flow may occur when gas flow dominates the multiphase flow in the pipe (and in mist flow, neither the water phase nor the oil phase is continuous). In such annular-mist flow, gas-carrying droplets of oil or water may move up the center of the pipe at high velocity while the remaining oil or water flows up along the pipe walls at low velocity.

In general, the liquid—which may be formed from multiple liquids mixed together—moves with a common velocity through the pipeline. However, in low flow velocity situations oil and water in the multiphase mixture may become partially or even completely separated. In such situations, the water and oil may travel at different velocities through the pipeline. For a non-horizontal pipe, the lighter oil may move up the pipe faster than the heavier water and causes small water drops to form that may in turn aggregate to form larger drops or slugs that may reach pipe diameter. This type of flow is often referred to as slug flow. The difference in velocity of the oil and water moving through the pipe is often referred to as "slip". Because gas has a substantially lower density than oil/water or a mixture of the two, a larger slip will occur between the gas and the liquid phases. This pseudo slug or slug flow can be met easily if there is a small diameter and in any type of angle if the capillarity effects are predominant.

These flow properties of the multiphase mixture in the pipeline may make it difficult to analyze the multiphase mixture and/or the properties of the different phases of the multiphase mixture. However, because of the importance of analysis of multiphase mixtures in the hydrocarbon industry, multiphase flow metering and the like has been growing rapidly and with this growth the need for analyzing problematic multiphase mixtures, such as mixtures with a high GVF up to wet gas conditions may be desirable. Measurements/analysis of problematic multiphase flows, such as wet gases and the like have been made possible by accepting some compromises in terms of accuracy on some parameters and the development of unique but expensive sensors. However, even with such compromises and/or use of expensive sensors prior systems may be unable to discriminate with a reasonable accuracy the three phases (gas, oil and water) flowing inside a pipe under conditions such as wet gas flow, high GVF and/or the like. In some cases, only gas/liquid or gas can be measured.

Taking an isokinetic sample of a multiphase mixture flowing through a pipeline may be a very challenging issue. Furthermore, subsequent analysis of the obtained isokinetic sample and/or retrieving a sample of one or more phases of the isokinetic sample may also be troublesome, especially in downhole and/or remote locations and may involve use of complicated and expensive devices, such as phase specific sensors, phase separators, processors for interpolating data obtained from mixed phases and/or the like.

SUMMARY OF THE INVENTION

This disclosure relates in general to systems and methods for analyzing multiphase flows containing one or more hydrocarbons flowing through a pipeline or the like. Embodiments of the present invention provide systems and methods for accurately and effectively measuring flow properties of phases of a multiphase mixture, sensing properties of phases of a multiphase mixture and/or collecting sample of phases of a multiphase mixture. More specifically, but not by way of limitation, embodiments of the present invention provide systems and methods for creating slug-type flows of isokinetically obtained samples of the multiphase mixture flow and analyzing/sampling the phases of the slug-type flow. In certain aspects, by spot checking particular phases of the slug-type flow of an isokinetically obtained sample of the multiphase flow, embodiments of the present invention may provide, among other things, for determining flow properties of gas, oil/condensate and/or water components of the multiphase flow. In other aspects of the present invention, by spot sampling particular phases of the slug-type flow, an active sampling device may be used to enrich one of the phases of the slug-type flow of the sampled multiphase mixture and/or take a representative sample of one of the phases of the slug-type flow of the sampled multiphase mixture.

In one embodiment of the present invention, a method for spot check analysis or spot sampling of a multiphase mixture flowing in a pipeline is provided comprising:

collecting a sample of the multiphase mixture under isokinetic conditions, wherein the multiphase mixture comprises a mixture of one or more different phases, and wherein a phase comprises one of a liquid phase, a gas phase, a water phase, an oil phase and an oil/condensate phase;

flowing the collected sample in a phase separated or slug-type flow; and detecting a presence of each phase of the one or more different phases of the phase separated or slug-type flow at a phase detection location.

And in a further embodiment, a system for spot check analysis or spot sampling of a multiphase mixture flowing in a pipeline is provided, comprising:

means for sampling the multiphase mixture under isokinetic conditions;

means for flowing the sample of the multiphase mixture in a phase separated or slug-type flow; and means for detecting a presence of a phase of the phase separated or slug-type flow at a phase detection location.

In certain aspects, by using temporal measurements in combination with the phase detection data, phase fractions of the different phases of the multiphase mixture may be determined. Furthermore, in certain aspects, the velocity of the multiphase mixture in the sampling conduit may be combined with the dimensions of the conduit to determine volume flow rates for the different phases of the multiphase mixture. And in certain embodiments, outputs from multiple phase detectors at different locations, may be cross-correlated to determine volume flow rates for the phases.

BRIEF DESCRIPTION OF THE DRAWINGS

In the figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

The invention will be better understood in the light of the following description of non-limiting and illustrative embodiments, given with reference to the accompanying drawings, in which:

FIG. 2A illustrates slug-type flow of an isokinetically obtained sample of a multiphase mixture through a sampling conduit, in accordance with an embodiment of the present invention;

FIG. 2B illustrates a further slug-type flow of an isokinetically obtained sample of a multiphase mixture through a sampling conduit, in accordance with an embodiment of the present invention;

DETAILED DESCRIPTION OF THE INVENTION

Embodiments of the present invention provide systems and methods for analyzing multiphase mixtures flowing in a pipeline. More specifically, but not by way of limitation, embodiments of the present invention provide systems and methods for obtaining, analyzing and/or sampling slug-type flows of isokinetically obtained samples of the multiphase mixture flowing in the pipeline. Certain embodiments of the present invention provide for spot checking of the slug-type flow of the isokinetically obtained sample that may provide for determining flow properties of gas, oil/condensate and/or water components of the multiphase mixture flowing in the pipeline. In certain aspects of the present invention, an active sampling device may be used to enrich one of the phases of the slug-type flow and/or take a representative sample of one of the phases of the slug-type flow.

Taking an isokinetic sample of a multiphase mixture flowing through a pipeline may be a very challenging issue. Furthermore, subsequent analysis of the isokinetic sample, flow characterization of the isokinetic sample and/or retrieving a sample of one or more phases of the isokinetic sample may be difficult and may involve use of complicated and expensive devices, such as phase specific sensors, phase separators and/or the like. Such issues may be even more severe in the hydrocarbon industry because pipelines transporting the multiphase mixtures of interest may be remote, downhole, subsea, associated with extreme conditions, not conducive to use with sensitive, expensive or interfering measurement/analysis/sampling systems and/or the like.

Figure 1:
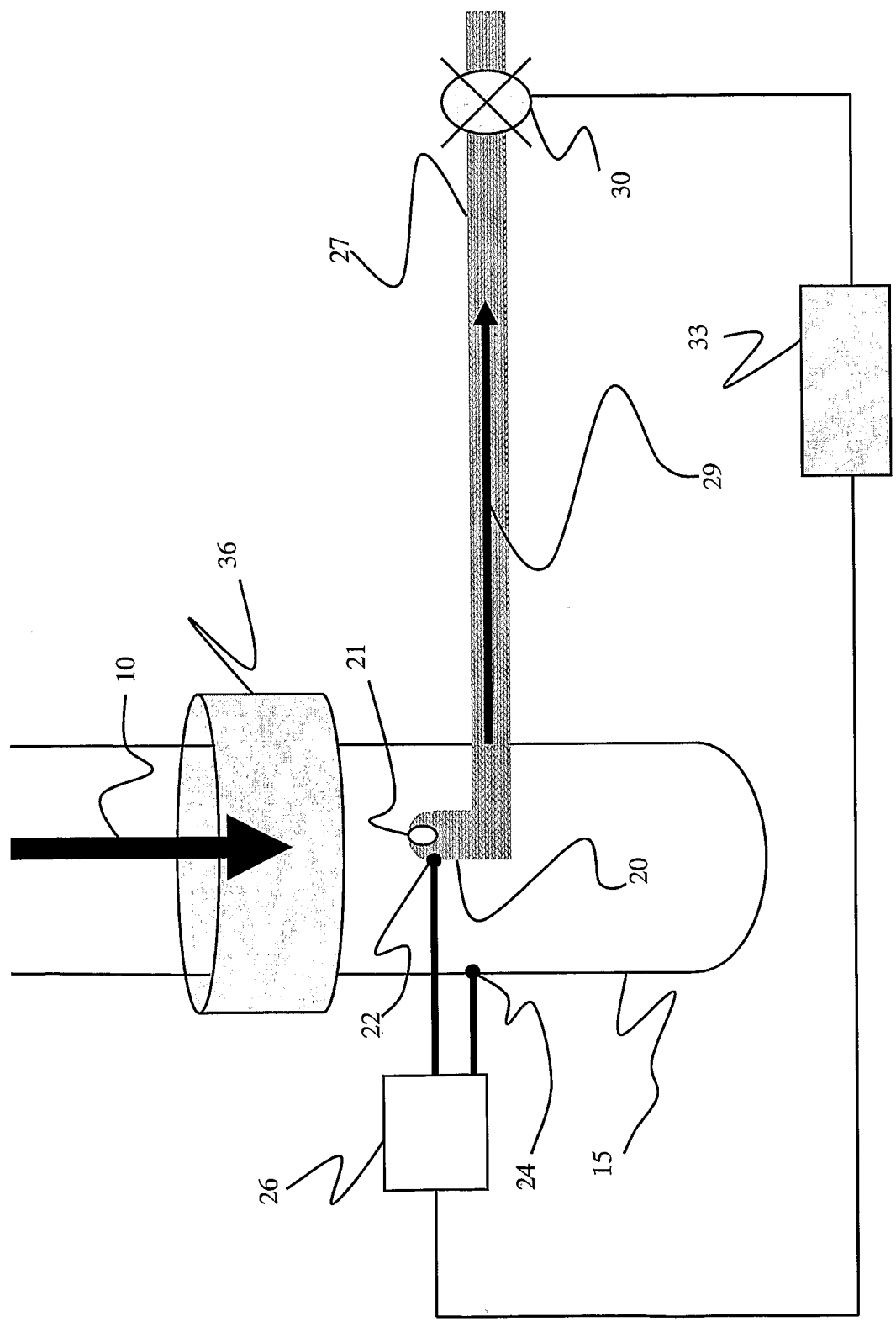
FIG. 1 is a schematic-type illustration of a system for providing phase distributed flow of an isokinetically obtained sample from a multiphase mixture flowing in a pipeline, in accordance with an embodiment of the present invention.

FIG. 1 is a schematic-type illustration of a system for providing phase distributed flow of an isokinetically obtained sample from a multiphase mixture flowing in a pipeline, in accordance with an embodiment of the present invention. As illustrated, a multiphase mixture 10 is flowing in a pipeline 15. The multiphase mixture 10 may contain one or more hydrocarbons, such as oil and/or gases such as ethane, methane or the like. The multiphase mixture 10 may include liquid phases, such as water or the like, gas phases, such as carbon dioxide or the like, and/or solid contaminants. The pipeline 15 may be a hydrocarbon transport pipeline, a pipeline associated with a wellbore penetrating an earth formation, a subsea pipeline and/or the like.

In an embodiment of the present invention, a sampling probe 20 may be positioned in the pipeline 15 and used to collect a portion of the multiphase mixture 10. A sampling probe opening 21 in the sampling probe 20 may allow a portion of the multiphase mixture 10 to flow through the sampling probe 20 into a sampling conduit 27. In an aspect of the present invention, during sampling of the multiphase mixture 10 a sample flow 29 may occur in the sampling conduit 27.

In certain embodiments of the present invention, a main flow pressure sensor probe 24 may be used to measure a pressure of the multiphase mixture 10 flowing in the pipeline 15 and a sample pressure sensor probe 22 may be used to measure a pressure of the sample of the multiphase mixture in the sampling probe 20. In different aspects of the present invention, the main flow pressure sensor probe 24 may be disposed at different locations in the pipeline 15 and the sample pressure sensor probe 22 may be disposed at different locations in the sampling probe 20 or the sampling conduit 27. The main flow pressure sensor probe 24 may be positioned at a sampling cross-section of the pipeline 15, where the sampling cross-section is essentially the cross-section of the pipeline 15 from which the sampling probe 20 collects a sample of the multiphase mixture 10. A differential pressure monitor 26 may be used to determine a differential pressure between the pressures measured by the main flow pressure sensor probe 24 and the sample pressure sensor probe 22.

A flow control valve 30 may be used to control the flow of the sample flow 29. In an embodiment of the present invention, the flow control valve 30 may be used to control the flow of the sample flow 29 to provide that the differential pressure between the pressures of the multiphase mixture 10 flowing in the pipeline 15 and the pressure of the sample flow 29 in the sampling conduit 27 is nulled and so provide for isokinetic sampling of the multiphase mixture. In certain aspects, a processor 33 may monitor the differential pressure determined by the differential pressure monitor 26 and may control the control valve 30 to provide for isokinetic sampling. The processor 33 may periodically or continuously adjust the control valve 30 to provide for the isokinetic sampling.

In some aspects of the present invention, a flow rate of the sample flow 29 may be measured by a flow meter (not shown). A second flow meter (not shown) may be used to measure a total flow rate of the multiphase mixture 10 in the pipeline 15. A ratio of the two measured flow rates may then be calculated. Based on this ratio, the sampling flow rate (i.e. the proportion of the fluid stream which is sampled) may be adjusted in order to substantially obtain isokinetic sampling conditions. This process may be repeated or carried out continuously throughout the sampling process to maintain isokinetic sampling of the multiphase mixture 10. In certain aspects, the flow control valve 30 may be used to adjust the flow rate of the sample flow 29 to provide for the isokinetic sampling.

In certain aspects, the sampled portion of the multiphase mixture may be analysed concurrently with the flow rate measurements and adjustments, for example to determine a gas/oil ration ("GOR"), a water/liquid ratio ("WLR") and samples for pressure/volume/temperature ("PVT") analysis may be obtained. This analysis may also use the flow rate measurement of the sampled portion.

To achieve good sampling of the multiphase mixture 10 a flow conditioner 36 may be used, such as the flow conditioner disclosed in the co-pending U.K. Patent Application No. 2406386A, the disclosure of which is hereby incorporated by reference. The flow conditioner 36 may be based on a combination of orifice plates with different beta ratios set at appropriate axial distances at a location in the pipeline upstream from the sampling probe 20. The flow conditioner 36 may have the functionality to keep the flow homogenous (in terms of liquid-gas velocities) at the sampling cross section. Flow conditioning may be achieved by different techniques, i.e. Venturi, mixing plate, choke and/or the like. In certain embodiments of the present invention, the differential pressure between the multiphase mixture 10 at the sampling cross-section of the pipeline 15 and the sample of the multiphase mixture in the sampling probe 20 and/or the sampling conduit 27 may be reduced to a strict minimum. In such embodiments, both the pressure and a temperature of the sample flow 29 may be maintained as close as possible to the pressure and temperature of the main stream flow, i.e. the flow of the multiphase mixture 10 in the pipeline 15. In this way, thermodynamic phenomena, such as hydrate formations, and the like may be avoided.

In embodiments of the present invention, isokinetic sampling may be performed for the purpose of obtaining a representative sample of the main flow of the multiphase mixture 10 flowing in the pipeline 15. In an embodiment of the present invention, the isokinetic sampling may provide that the right proportions of each phase of the multiphase mixture may be sampled through the sampling probe 20 into the sampling conduit 27. In embodiments of the present invention, the isokinetic sampling may provide that a velocity of the sample flow 29 at the sampling probe opening 21 may be the same as the velocity of the multiphase mixture 10 flowing in the in pipeline 15, at the upstream of the sampling probe opening 21.

In an embodiment of the present invention, the sampling conduit 27 may be configured to provide that the sample flow 29 may flow through the sampling conduit 27 such that there is separation between the phases of the multiphase sample flowing in the sampling conduit 27; this phase separated flow may be referred to as slug flow, slug-type flow and/or the like. In certain embodiments of the present invention, the diameter of the sampling conduit 27 may be selected to provide that phase separation occurs and/or is maintained in the sampling conduit 27. In embodiments of the present invention, the sampling conduit 27 may have a small diameter to provide that capillary effects dominate the sample flow 29 in the sampling conduit 27 and cause slug-type flow of the sample through the sampling conduit 27. Merely by way of example, in certain aspects of the present invention, the sampling conduit 27 may have an internal diameter in the range of 10 s of millimetres, less than 10 millimetres or the like.

FIG. 2A illustrates slug-type flow of an isokinetically obtained sample of a multiphase mixture through a sampling conduit, in accordance with an embodiment of the present invention. In an embodiment of the present invention, capillary effects in the sampling conduit 27 may be used to attain/maintain the slug-type flow of the sample in the sampling conduit 27 downstream of where the sample of the multiphase mixture is retrieved from the main pipeline.

In an embodiment of the present invention, the sampling conduit 27 may have an internal diameter 40 that is small enough to provide that the capillary effects result in the sample flow 29 flowing as separated phases through the sampling conduit 27. In certain aspects of the present invention, the capillary effect may cause the sample flow 29 to flow in a slug-type flow with a liquid phase of the sampled multiphase mixture flowing as liquid slugs 50 in the sampling conduit 27. The liquid slugs 50 may comprise water, oil/condensate and/or the like. The liquid slugs 50 may flow through the sampling conduit 27 separate from gas phase areas of flow 53. The gas phase areas of flow 53 may comprise gaseous hydrocarbons, carbon dioxide, hydrogen, hydrogen sulphide and/or the like.

FIG. 2B illustrates a further slug-type flow of an isokinetically obtained sample of a multiphase mixture through a sampling conduit, in accordance with an embodiment of the present invention. In certain aspects of the present invention, the capillary effects may provide that the one or more liquid components of the sampled multiphase mixture may flow through the sampling conduit 27 separately from one another.

Merely by way of example, water slugs 51, oil slugs 56 and/or the like may flow through the sampling conduit 27 as separated slugs in the overall sample flow. The water slugs 51 may comprise primarily water and the oil slugs may comprise primarily oil. The gas phase areas of flow 53 may flow with the water slugs 51, the oil slugs 56 and/or the like through the sampling conduit 27.

Figure 3:
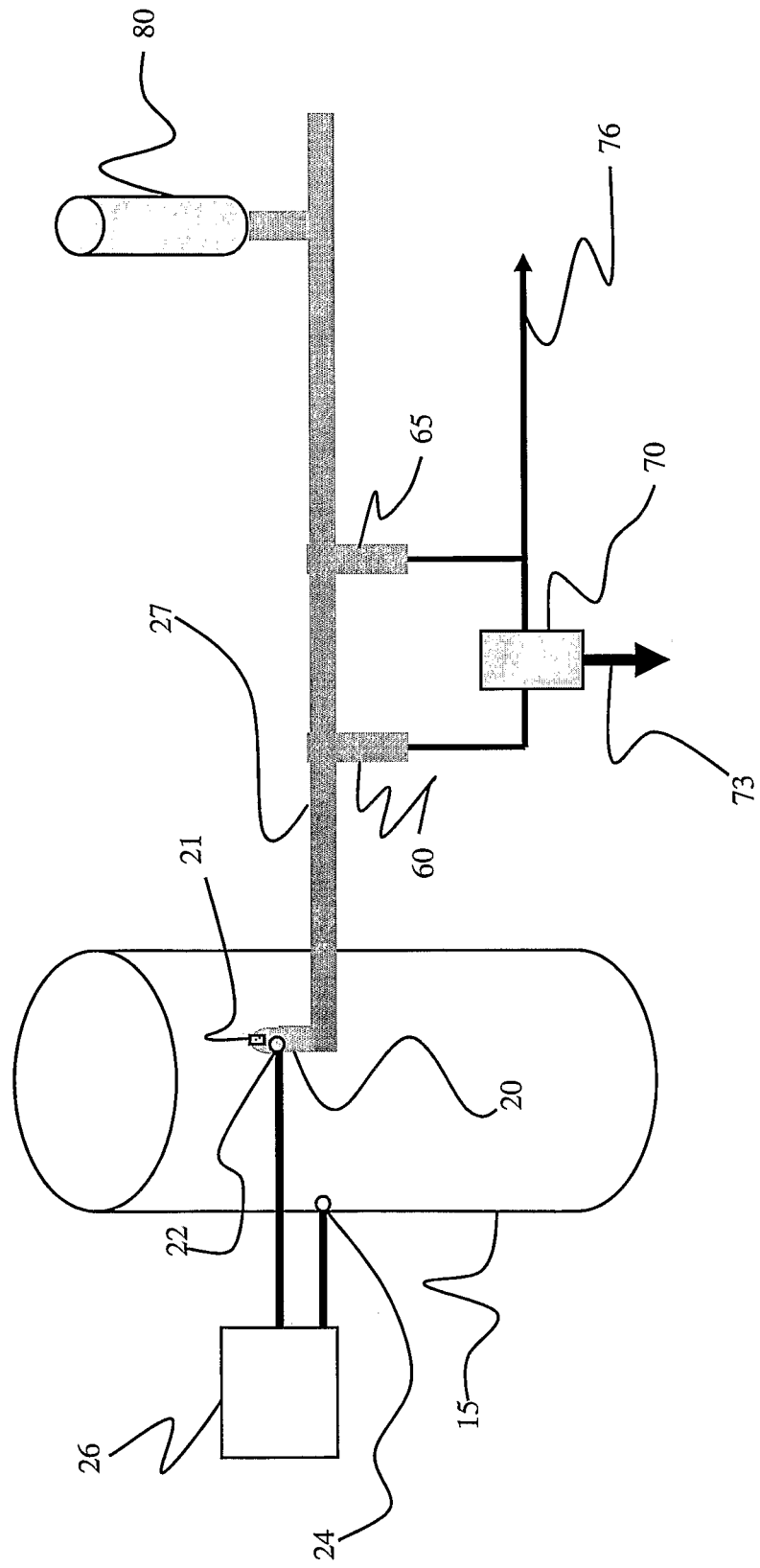
FIG. 3 is a schematic-type illustration of a system for spot-check phase detection of a phase distributed flow of an isokinetically obtained sample from a multiphase mixture flowing in a pipeline, in accordance with an embodiment of the present invention.

FIG. 3 is a schematic-type illustration of a system for spot-check phase detection of a phase distributed flow of an isokinetically obtained sample from a multiphase mixture flowing in a pipeline, in accordance with an embodiment of the present invention. In an embodiment of the present invention, the sampling probe 20 may be configured with the sampling probe opening 21 having an internal diameter or the like of the order of millimetres. Merely by way of example, in certain aspects of the present invention the sampling probe opening 21 may having an internal diameter in a range of 1-5 mm or the like and the sampling probe 20 may have an internal diameter in a range of around 5-10 mm. In other aspects of the present invention, the sampling probe 20 may have an internal diameter in a range from 1 mm to tenths of millimetres.

The main pipe in which the multiphase mixture is flowing may have a much larger internal diameter. Merely by way of example, the main pipe may have an internal diameter of a 100 mm or greater. In certain embodiments of the present invention, the sampling conduit 27 may have an internal diameter that is less than about 10 mm. In such embodiments, the small internal diameter of the sampling conduit 27 downstream of the sampling probe 20 may cause capillarity effects to affect the flow of the isokinetically obtained samples of the multiphase mixture and may provide that the flow of the isokinetic sample of the multiphase mixture in the sampling conduit 27 is, as described above, essentially sluggy, such as gas pockets followed by liquid, oil and/or water slugs.

In embodiments of the present invention, the phase separated flow of the isokinetically obtained sample in the sampling conduit 27 may be spot analysed, measured and/or sampled to determine flow properties of the multiphase mixture flowing in the main pipeline. In certain aspects, a phase detector 60 that may be capable of distinguishing between two or more phases flowing in the sampling conduit 27 may be used for spot analysis of the phase separated sample. The phase detector 60 may provide for real-time identification of phases flowing in the sampling conduit 27. The phase detector 60 may be an optical reflectance (refractive-index) discrimination probe, an optical fluid analyzer (e.g. based on absorption measurements at multiple wavelengths), an electrical impedance (conductance and/or capacitance) sensor, a microwave (resonance, reflection or transmission) device, a millimetre-wave sensor, an acoustic sensor, a nuclear densitometer, a spectral analyzer and/or the like.

By distinguishing the different phases flowing in the sampling conduit, one or more analysis methods may be used in conjunction with the phase detector 60, such as nuclear measurements, optical measurements, Coriolis measurements, flow measurements and/or the like, to determine properties of one or more of the separated phases flowing in the sampling conduit 27. By maintaining separation of the phases, the present invention provides for efficient and effective analysis of the multiphase mixture. Merely by way of example, in an embodiment of the present invention, the phase detector 60 may identify the presence in real-time of a particular phase in the sampling conduit 27 and a spot analysis method may then be applied to this particular phase. In this way, aspects of the present invention, because they identify single phases in the sampling conduit, remove the need to determine amounts of different phases in a sample being analyzed. In such aspects, the present invention provide for spot check analysis of particular separated phases of a sample of a multiphase mixture flowing in a pipeline.

In other embodiments of the present invention, by identifying the separated phases in the sampling conduit, continuous/periodic spot check measurements may be made regarding flow properties of the particular phase. For example, in some embodiments, the phase detector 60 may comprise an optical fluid analyzer or the like and may identify water slugs flowing in the sampling conduit 27. From temporal (time-continuous) measurements regarding water slug detection by the phase detector 60, a determination regarding a relative amount of water in the flowing sample may be found. This determination may be used to interpolate a water fraction in the sample and a water fraction in the flow of the multiphase mixture in the main pipeline. Similarly, an oil fraction, a gas fraction and/or the like for the flowing sample and the main flow in the main pipeline may be determined using the phase detector 60 and temporal (time-continuous) measurements regarding detection of the phases of the sample flow.

In other aspects, temporal (time-continuous) determinations regarding the fraction of different phases in the flowing sample may be combined with the velocity data of the sample in the sampling conduit 27 to determine volumetric flow rates and/or the like of one or more phases in the sampling conduit and, consequently because of the isokinetic sampling conditions, volumetric flow rates and/or the like of one or more phases in the main pipeline (after scaling up by the cross-sectional area ratio of the main pipeline 15 to the sampling probe opening 21). By processing with the mass density data from other sensors or from known inputs, mass flow rates or the like of different phases of the multiphase mixture in the sampling conduit and the main pipeline may be determined (after the scaling up described above).

In some embodiments, a second phase detector 65 may be used to detect phases of the multiphase sample at a second location in the sampling conduit 27. In such embodiments, outputs from the phase detector 60 and the second phase detector 65 may be input into a processor 70 that may cross-correlate the data from the two phase detectors to determine slug flow velocity and hence the volumetric flow rates for one or more phases of the multiphase sample (together with the measured sample phase fractions) and, because of isokinetic sampling, the multiphase mixture in the main pipeline. The cross-correlation processing may use the separation between the phase detectors and the relative outputs from the two devices to determine the flow velocity.

In certain aspects, the processor 70 may output processing data 73 that may be used in combination with measurements from other devices associated with the sampling conduit 27 or the main pipeline to analyze the flow properties of the multiphase mixture. In other aspects, the processor 70 may use a control signal 76 or the like to activate a sampling device 80 to collect a sample of a particular phase from the sampling conduit 27. Merely by way of example, by determining a presence of a particular phase at a location of a phase detector, from the location of the sampling device 80 and velocity measurements of the flow of the sample, the processor can determine when to activate the sampling device 80 to sample only a particular phase.

Figure 4A:
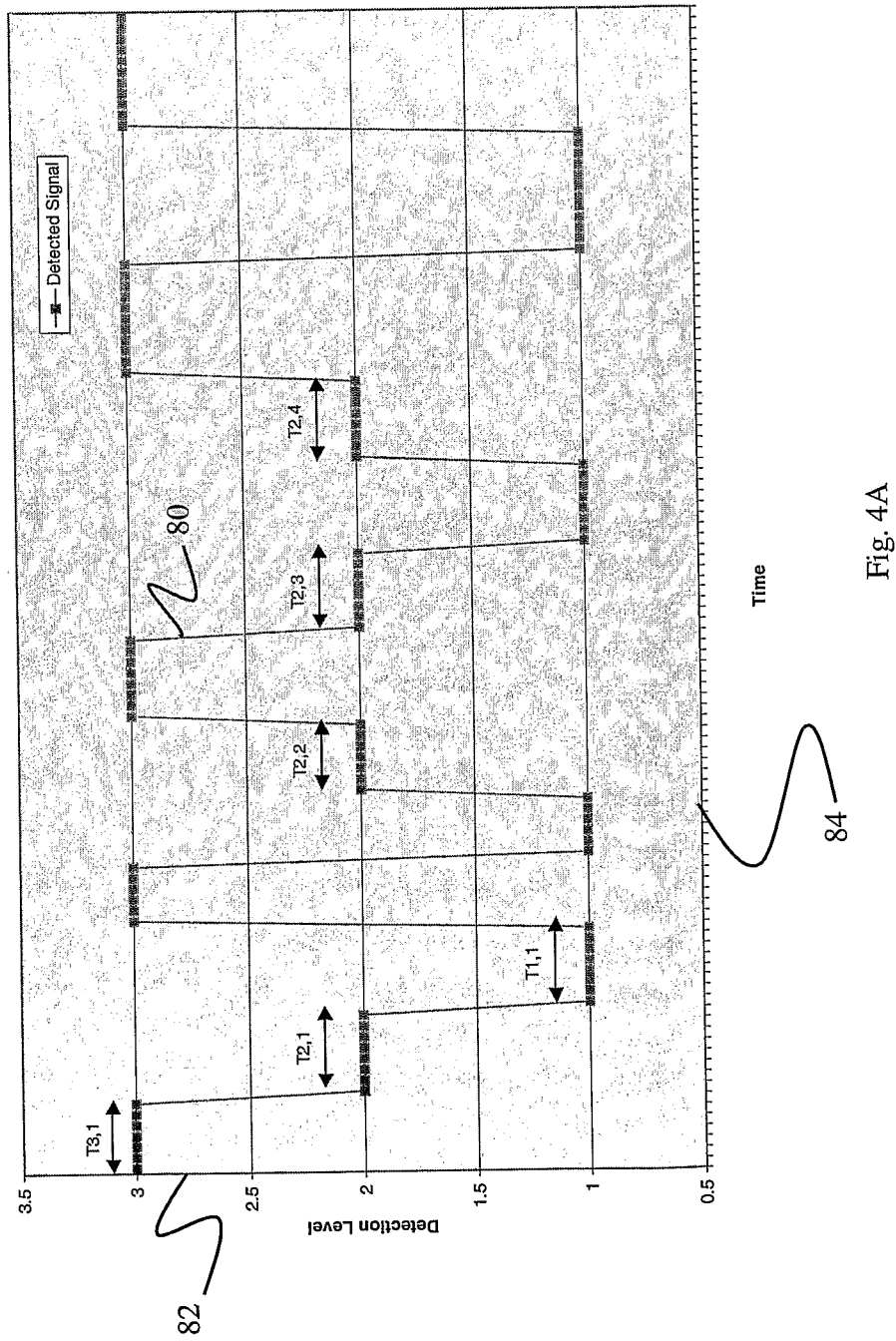
FIG. 4A illustrates detection output over time from a phase detector detecting phase data from a slug-type flow from a sample of a multiphase mixture flowing in a pipeline, the sample taken under isokinetic conditions, in accordance with an embodiment of the present invention.

FIG. 4A illustrates detection output over time from e.g., an optical phase detector detecting phase data from a slug-type flow from a sample of a multiphase mixture flowing in a pipeline, the sample taken under isokinetic conditions, in accordance with an embodiment of the present invention. In certain aspects, an optical phase detector such as disclosed in co-pending Patent Application No. WO2006005600A1 may be used, the disclosure of which is hereby incorporated by reference. As illustrated, an output from an optical phase detector 81 is plotted on a detection output axis 82 and a time axis 84. As depicted, the optical phase detector may provides a different output relative to the different phases it detects—for example, this may be due to the differences in the refractive index n of gas (n=1.0-1.1), condensate/oil (n=1.4-1.5) and water (n ~1.33)).

In one embodiment of the present invention, the sample may contain three fluids water, oil/condensate as well as a gas phase. In an embodiment of the present invention, a fraction of each liquid phase and/or the gas phase may be determined by using the time-continuous measurement. For example, by defining Ti,j as a period when a detection level was equal to 'i', where i corresponds to one of the liquid phases or a gas phase (oil/condensate, water or gas) and j corresponds to a sequence in the overall recording signal, the fraction of each phase may be calculated as follows:

$$Fr_i = \frac{\sum_j T_{i,j}}{\sum_i \sum_j T_{i,j}} \quad (1)$$

Figure 4B:
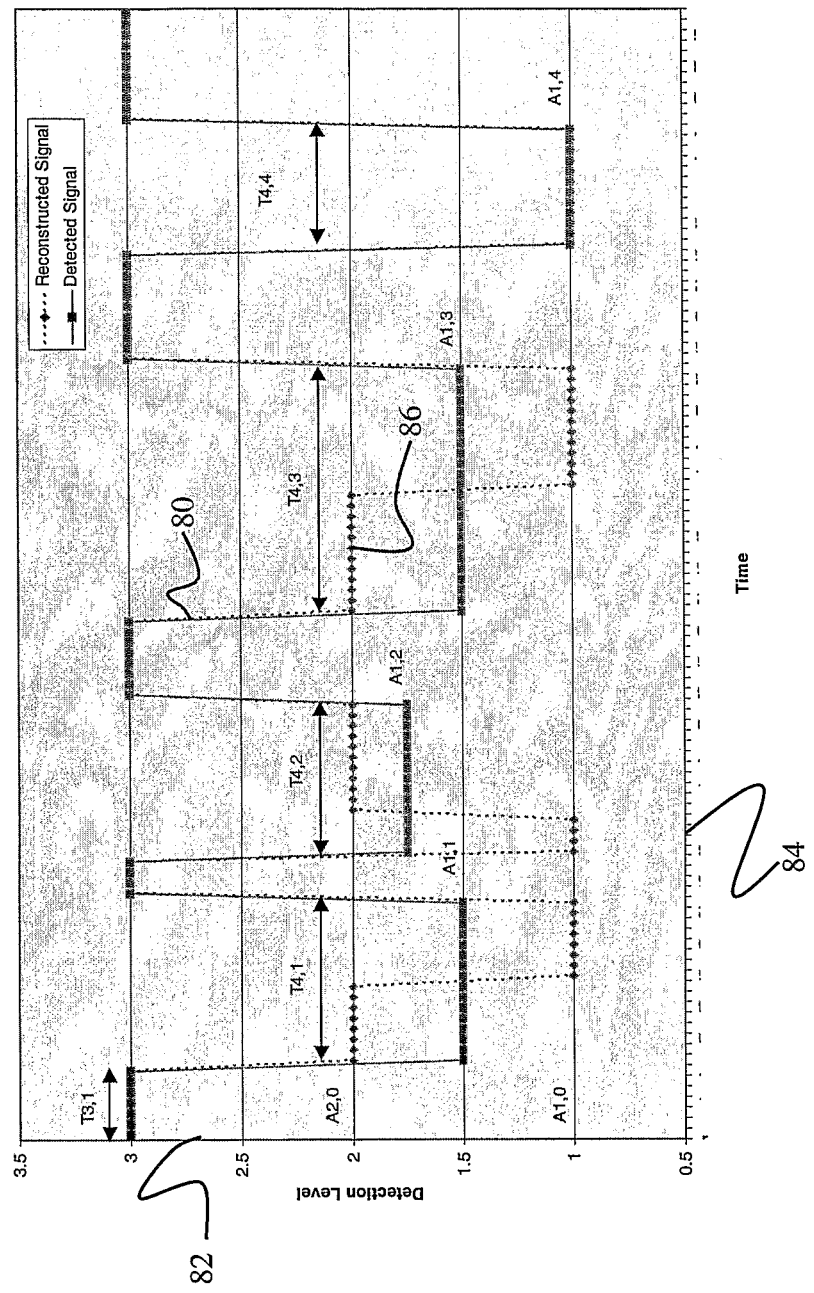
FIG. 4B illustrates detection output over time from a phase detector detecting phase data from a slug-type flow from a sample of a multiphase mixture flowing in a pipeline, the sample taken under isokinetic conditions, and a reconstructed output using amplitude data to correct for water/oil emulsions, in accordance with an embodiment of the present invention.

FIG. 4B illustrates detection output over time from a phase detector detecting phase data from a slug-type flow from a sample of a multiphase mixture flowing in a pipeline, the sample taken under isokinetic conditions, and a reconstructed output using amplitude data to correct for water/oil emulsions, in accordance with an embodiment of the present invention. As depicted, an output from a phase detector 81 is plotted on a detection output axis 82 and a time axis 84. A reconstructed output 86 illustrates a corrected output from the phase detector that is corrected for emulsions formed between water and oil in the phase separated sample.

In the case of an emulsion forming, i.e. mixing of different liquid phases such as mixing of oil, condensate and/or water, in an embodiment of the present invention, the amplitude of the signal from the phase detector may be used as follows to correct for emulsification and provide for obtaining correctly the different fractions of the phases in the sample (based upon an assumption in the illustrated FIG. 4B that detection output 1 and 2 are for the oil and water phases, respectively). The emulsification correction may be determined from the following:

$$T_{1,k} = \frac{A_{1,k} - A_{2,0}}{A_{1,0} - A_{2,0}} \cdot T_{4,k} \text{ and } T_{2,k} = \frac{A_{1,k} - A_{1,0}}{A_{2,0} - A_{1,0}} \cdot T_{4,k} \quad (2)$$

In such aspects, the reconstructed output 86 may be obtained and, as such, the provisions of equation (1) may be applied to the reconstructed data to determine phase fractions. In different aspects, different types of processing of the output from the phase detector 60 and or the second phase detector 65 may be used to obtain fraction calculations.

In certain embodiments, it may be possible to calculate different ratios of different phases and different components of different phases at line conditions and in many types of situation in a straightforward manner without taking into account velocity slip etc because of the isokinetic conditions the sample is taken under. In other word, problems associated with slippage, which may include challenging modeling of the different phases under the prevailing conditions with uncertainties due to the impossibility to measure cut and holdup at the same time for the different phases may be resolved using an embodiment of the present invention.

In aspects of the present invention:
The Water Liquid Ratio ("WLR") may be defined by:

$$WLR = \frac{Fr_{water}}{Fr_{water} + Fr_{oil}} = \frac{\alpha_{water(time)}}{\alpha_{liquid(time)}}$$

The Gas Oil/Condensate Ratio ("GOR") may be expressed as:

$$GOR_l = \frac{Fr_{gas}}{Fr_{oil}} = \frac{\alpha_{gas(time)}}{\alpha_{oil(time)}}$$

The Gas Liquid Ratio ("GLR") may be obtained from:

$$GLR = \frac{Fr_{gas}}{Fr_{water} + Fr_{oil}} = \frac{\alpha_{gas(time)}}{\alpha_{liquid(time)}}$$

Moreover and by construction, in an embodiment of the present invention the sample may be taken under isokinetic conditions, where the velocity of the sample (at the sampling probe opening 21 in FIG. 1) is identical to the velocity of the multiphase mixture in the main flow and, furthermore, the flow may be homogenous due to use of flow conditioner before sampling. In such aspects it may be possible to calculate a flow rate for the different phases and different liquid phases.

Defining $A_{pipe}$ as the main flow line cross-sectional area, $A_{probe}$ as the probe flow line cross-sectional area collecting the isokinetic sample, $Q_{total-pipe}$ as the total volumetric flow rate in the main pipe, $Q_{total-probe}$ as the total flow rate flowing inside the probe. Under the condition of negligible pressure loss up to the sampling flow line where the sample flow velocity measurement is made, in an aspect of the present invention it may be possible to write the following expression for the total volume flow rate, liquid volume flow rate, and gas, water and oil volume flow rates based on the previous calculation of the different fractions, as follows:

$$Q_{Total-pipe} = \frac{A_{pipe}}{A_{probe}} Q_{Total-probe}$$

$$Q_{Gas-pipe} = \frac{GLR}{GLR + 1} Q_{Total-pipe}$$

$$Q_{Water-pipe} = \frac{WLR}{GLR + 1} Q_{Total-pipe}$$

$$Q_{Oil-pipe} = \frac{1 - WLR}{GLR + 1} Q_{Total-pipe}$$

$$Q_{Liq-pipe} = \frac{1}{GLR + 1} Q_{Total-pipe}$$

In certain embodiments, these equations may be solved by a processor or the like when a $Q_{total-probe}$ flow rate is measured.

As provided above, in an embodiment of the present invention, by using an appropriate piping size for the sampling flow line, it is possible to produce a slug flow in the sampling flow line, the capillarity effect being the main driver and no segregation of the different phases may be experienced, i.e. no stratified flow. In certain aspects of the present invention, a volumetric flow rate may be determined by cross correlation. In such aspects, by measuring a time shift Δt between two identical sensors and knowing accurately the distance L between the sensors, the volumetric flow rate may be determined from the following:

$$Q_{Total-probe} = \frac{L}{\Delta t} \times A_{probe}$$

In different aspects of the present invention, various types of sensors may be used to determine a cross correlation velocity measurement, such sensors may include optical, electrical impedance (conductance and/or capacitance), microwave (transmission, reflection, resonance), millimetre-wave, acoustic and the like.

Figure 4C:
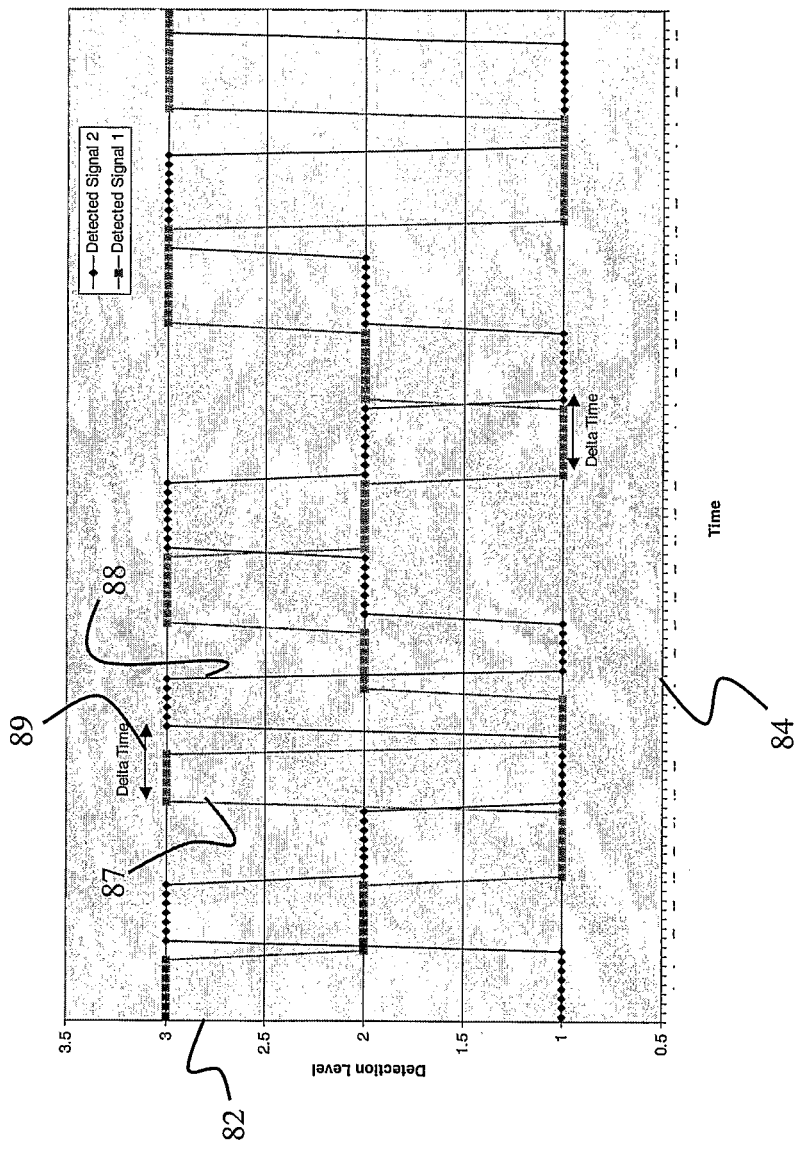
FIG. 4C illustrates cross-correlation of output data from a pair of phase detectors at separate locations detecting phase data from a slug-type flow from a sample of a multiphase mixture flowing in a pipeline, the sample taken under isokinetic conditions, in accordance with an embodiment of the present invention.

FIG. 4C illustrates a cross correlation representation based on an output from two identical sensors detecting presence of a phase at the sensor location in a sampling flow line with slug-type flow of a sample obtained under isokinetic conditions, in accordance with an embodiment of the present invention. In one embodiment, two optical phase detectors may be used to determine the presence of a phase—a gas phase, a liquid phase, a water phase, an oil phase and/or the like—at the sensor's location along the sample flow line.

In FIG. 4C an output 87 from a first phase detector and an output 88 from a second phase detector at two locations on a sampling conduit are both plotted on a graph of a detection output axis 82 versus a time axis 84. A time delta 89 is a difference in time between a detection of the same phase by the two phase detectors due to the time it takes the phase, to travel from the first phase detector to the second phase detector. In aspects of the present invention, using discrimination of the different phases, without the need for special calibration or maintenance, embodiments of the present invention may use a Fast Fourier Transform or similar signal processing operator to obtain the time shift between both sensors shown in FIG. 4C.

In conjunction with the phase detector(s), an additional classical mass flow meter or a similar instrument for measuring single-phase flow or the like may be used when the phase detector determines that one of the phases is much larger in volume or mass than the others. In certain embodiments, the second phase detector sensor may be used to determine cross-correlation velocity, for redundancy measurements to verify the different fractions calculated by the first system and/or the like.

Under isokinetic sampling conditions, a fluid velocity of the sample at the opening of the sampling probe will be identical to the velocity of the multiphase mixture flow in the main pipe at the probe-opening upstream. This velocity may be above a velocity of 10 meter/second. In certain aspects, the velocity of the sample in the sampling conduit may be decreased by increasing the diameter of the sampling conduit downstream of the sample probe opening. In such aspects, the velocity will be reduced by the square of the ratio of both diameters, the diameter at the opening and the diameter at the increased-diameter sampling conduit. Merely by way of example, if the diameter of the probe opening is smaller than 2 mm and a diameter of the sampling conduit downstream of the sampling probe is around 6 mm then the velocity may be reduced by a factor of 9 in the sampling conduit. In aspects of the present invention, selecting an internal diameter for the sampling conduit or using a device to control the internal diameter may be used to control the velocity of the sample for measurement purposes. Moreover, in certain embodiments of the present invention to reduce the flow velocity of the sample several sampling conduits may be used to provide that velocity of the sample is reduced, but slug-type flow in the sampling conduits is maintained by capillary effects.

In certain aspects, reducing the velocity of the sample flow may be used to decrease frictional pressure loss of the sample inside the sample piping. Pressure loss per unit length of the sample piping may be approximated by the following expression:

$$Pf = f \cdot \rho_h \cdot u_h^2 / r$$

with $\rho_h$ being the homogeneous density, $u_h$ the homogeneous velocity, f the fanning factor and r the radius of the pipe. Assuming $Pf_1$, $Pf_2$ the pressure loss for a given condition with respectively a radius $r_1$ and $r_2$ then:

$$\frac{Pf_1}{Pf_2} = \left(\frac{r_2}{r_1}\right)^{4.75}$$

Merely by way of example, in an embodiment with a sampling probe opening of 2 mm and a sampling conduit of 6 mm, the ratio is equal to 184.6 providing that pressure loss is reduced in such an embodiment by a factor 180.

In an embodiment of the present invention, internal diameter of the sampling conduit(s) or use of multiple conduits may be used to keep the pressure loss low and, as a result, provide for a minimum difference of pressure between the fluid sample in the sampling conduit and the multiphase mixture in the main pipeline at the sampling location. In such an embodiment, assuming the sample in the sampling conduit is maintained at a temperature similar to the multiphase mixture, the volumetric flow rates of different phases of the multiphase mixture in the main pipe may be calculated without inputs related to fluid properties. As such, calibration, including in-situ calibration, may not be required in embodiments of the present invention, In an embodiment of the present invention, because of a significantly reduced calibration requirement, a flow analyzer may be configured as a "plug and play" device that may be fabricated and installed into pipelines without consideration of relative properties of the pipeline or the multiphase mixture flowing in the pipeline. In certain aspects, such a device may be implemented subsea with the use of flow control valves to adjust isokinetic conditions. For well testing, a probe in accordance with an embodiment of the present invention may be used as a spot check system and temporarily installed to measure flow rate and then removed. Such embodiments may be used in maintenance projects on pipelines for transporting hydrocarbons. With the probe dimension being small, it may be possible in certain aspects to do this type of operation with an appropriate sealing mechanism without stopping the main flow production of hydrocarbons through the pipeline being monitored.

In some aspects of the present invention, the sampling probe may traverse over a diameter path in the pipeline to obtain samples/data at different locations across the internal diameter of the pipeline. In such aspects, by using the sample probe in a pilot mode, i.e. closing a valve downstream of the probe, an impact pressure of the multiphase mixture in the pipeline may be determined that is related to the velocity and density of the mixture and may allow a profile of the multiphase mixture flow to be determined and to check in real time if the flow is in a homogenous condition.

In embodiments of the present invention, because the volume of the sample necessary for a measurement is small, the embodiments of the present invention may be applied to a wide range of pressures and temperatures with standard piping dimensions, and a minimum of engineering development for most of the mechanical parts. Further, in certain embodiments of the present invention, because the flow rate is relatively small in the sample piping and the phase detection probes are not in contact with the main flow, the reliability of embodiments is high. Moreover, in embodiments of the present invention, the probes may be continuously wiped by the slugs preventing unwanted build up on the sensors and providing long term accuracy. However, even if a deposit such as asphalten is deposited on a sensor, in an embodiment of the present invention, signal amplitude monitoring and interpretation may be used to correct for the effect of the deposit and maintain the accuracy of the measurements. To make the system rugged, the sampling probe may be designed to withstand the different conditions, including flows with debris or solid particles such as sand.

By having a fluid at temperature and pressure in the sampling conduit approximating that of the conditions in the main pipeline, in some embodiments of the present invention, a representative sample of the multiphase mixture may be obtained from the sampling conduit and analysis, measuring and/or the like of such a sample may provide for determining different fluid properties of the multiphase mixture flowing in the main pipeline. In such embodiments, there may be no need of recombination of the sample, determining information regarding the sampling process such as CGR, GOR and/or the like. Furthermore, in such embodiments, the sample handling process may be simplified and the sampling process may be easily controllable by a control processor or the like to capture an appropriate amount of sample, to retrieve a sample under specified conditions and/or the like.

In certain embodiments of the present invention, the systems and methods may be configured for continuous mode operation, i.e. samples of the multiphase mixture may be continuously/repeatedly circulating through the system. In certain aspects of the present invention, a return line/pipe may be used to circulate samples through the system and back into the main pipeline. A pressure differential between the tip of the sampling probe and the return line may be used to provide for circulation through the system. In certain aspects, circulating the sample may provide for returning the sample to the main pipeline downstream of the sampling probe after an elbow or any equipment generating a sufficient pressure drop. In other aspects, the sample may be re-injected into the main pipe using a venturi or differential pressure device to provide for the re-injection. In some embodiments, sampling from the main pipeline and/or the sampling line/conduit may be provided using a cylinder with a control system so as to collect the fluid under pressure.

In certain embodiments, the main fluid flow of the multiphase mixture through the main pipe may be used to heat the system, including the sampling conduit, to provide for mirroring conditions in the system to those existing in the main pipe. Insulation or the like may be used to prevent temperature loss from the system.

Figure 5:
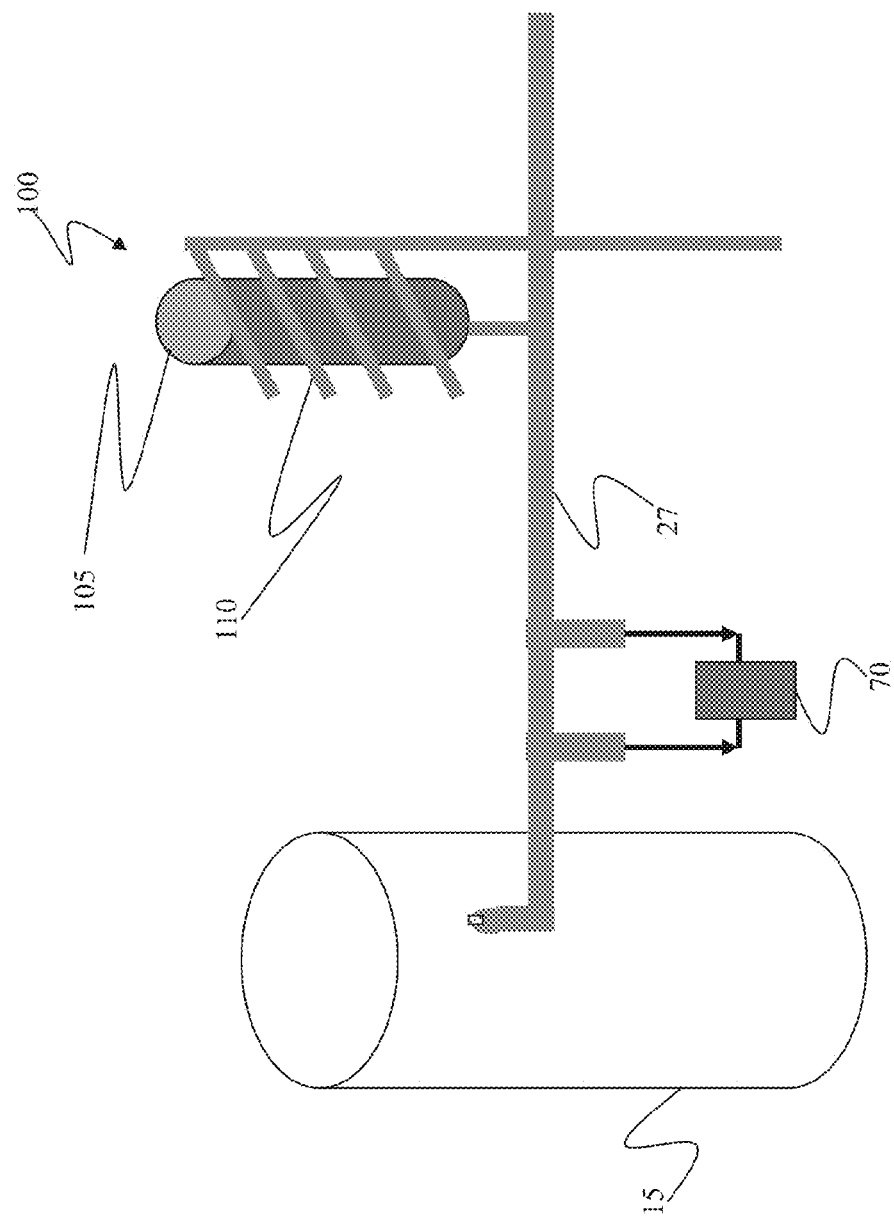
FIG. 5 is a schematic-type illustration of a system for spot sampling one or more phases of a phase distributed flow of an isokinetically obtained sample from a multiphase mixture flowing in a pipeline, in accordance with an embodiment of the present invention.

FIG. 5 is a schematic-type illustration of a system for spot sampling one or more phases of a phase distributed flow of an isokinetically obtained sample from a multiphase mixture flowing in a pipeline, in accordance with an embodiment of the present invention. In some embodiments, enrichment of a specific phase may be performed prior to analysis of the phase. As observed previously, embodiments of the present invention provide for determining the flow rate of different phases, such as gas, liquid, water, oil etc., of the multiphase at line conditions without a need for obtaining information about the fluid properties.

However, it may be necessary, desirable to check the fluid properties. As such, in certain aspects, a sampling device may be coupled with the sampling conduit 27. Merely by way of example, in certain aspects, an active sampling device 100 may be used to obtain such samples. The active sampling device 100 may be a processor controlled device that is configured for selective control of the samples being collected, for example samples of single phases may be collected, samples may be collected when certain conditions in the main pipeline 15 or the sampling conduit 27 occur and/or the like.

Merely by way of example, the active sampling device 100 may comprise a piston chamber 105 with a simple manifold (not shown). Such a device may provide for segregation of the different phases and/or maintaining a selected phase for transfer to a sampling bottle for analysis at the well site. In certain aspects, to provide for capture of the relevant phase by the active sampling device 100, determination of the properties of the fluid flowing towards an analysis kit and/or a sampling bottle may be necessary. As such, the phase detector 70, which may be an optical phase detector or the like, may be used to verify the type/quality of the sample prior to analysis. In certain aspects, a sample of the multiphase mixture from the main pipeline 15 may be circulated through a heating element 110 to warm the active sampling device 100. Using a temperature sensor, such as a thermocouple or the like, sampling by the active sampling device 100 may occur when the temperature of the active sampling device 100 has reached a determined value. The active sampling device 100 may comprise a hand pumping system, a hydraulic pumping system and/or the like and may provide for collecting the different phases for the determination of the typical parameters such as volume and expansion factors, dissolved gas or condensate in each phase, or the different densities at line or standard conditions and/or the like. The active sampling device 100 may comprise an active sampling device such as the one disclosed in the co-pending Patent Application No. WO2006037565A1, the disclosure of which is hereby incorporated by reference.

Embodiments of the present invention, provide systems and methods for analyzing flow rates and fractions of individual phases, such as liquid, gas, water and/or oil phases of a multiphase mixture flowing in a pipeline in which no knowledge of the fluid properties is necessary. Certain aspects provide for, amongst other things, flow rate and fraction analysis of phases with a reduced requirement of knowledge of fluid mechanics, avoiding the issues related to flow-velocity slip models and the tuning of empirical parameters.

Certain embodiments of the present invention may be used as a flow meter that may be used with any type of multiphase mixture including but not limited to high GVF to wet gas conditions (GVF>92%). With adequate mechanical sealing in place, an embodiment of the present invention may be inserted in any type of pipeline without stopping the main production and may be used in a subsea condition by ROV intervention or in continuous mode.

Figure 6:
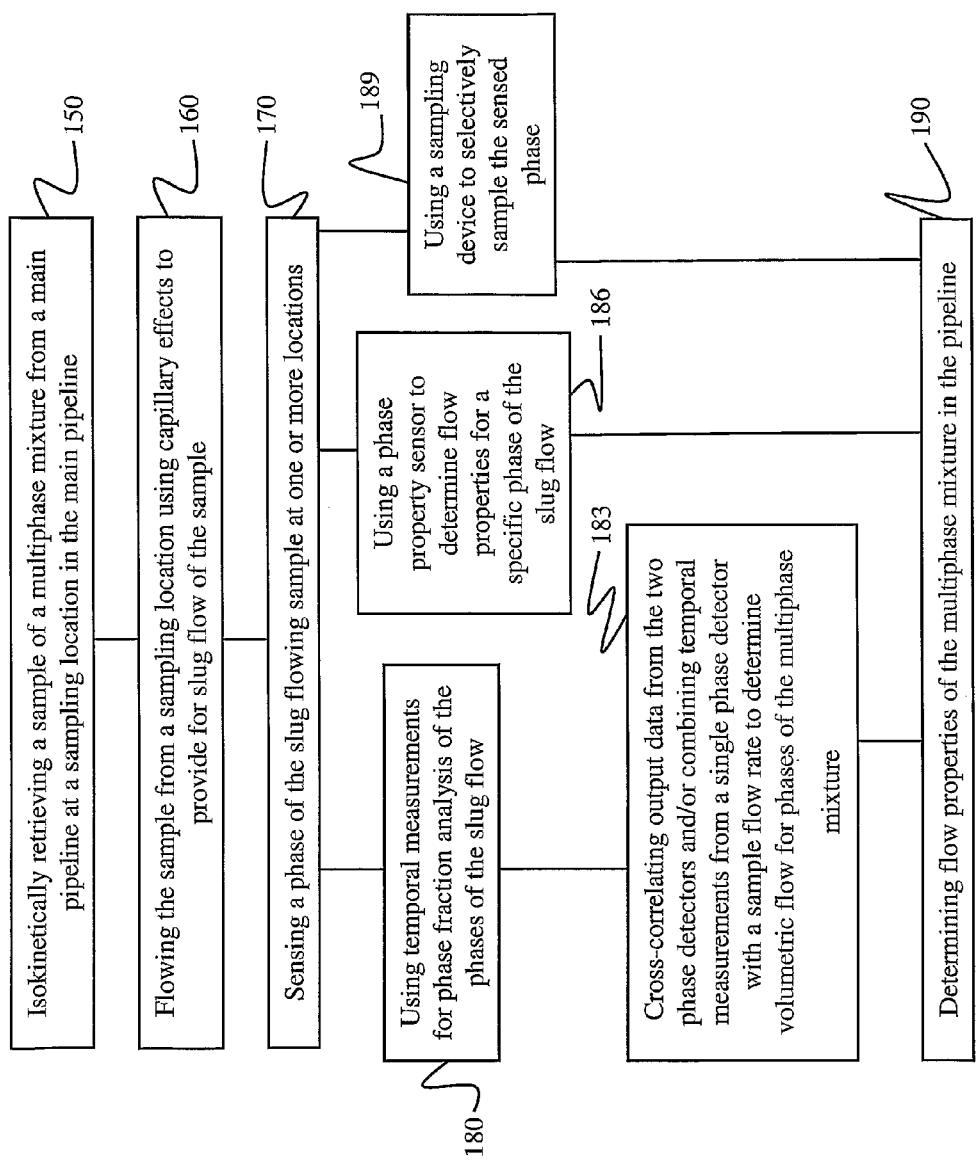
FIG. 6 is a flow-type representation of a process for spot phase detection, spot analysis and/or spot sampling of one or more phases of a phase distributed flow of an isokinetic sample of a multiphase mixture flowing in a pipeline, in accordance with an embodiment of the present invention.

FIG. 6 is a flow-type representation of a process for spot checking and/or sampling one or more phases of a phase distributed flow of an isokinetic sample of a multiphase mixture flowing in a pipeline, in accordance with an embodiment of the present invention. In step 150, a sample of a multiphase mixture from a main pipeline at a sampling location in a main pipeline is taken under isokinetic conditions. To obtain the sample under isokinetic conditions, a pressure of the multiphase mixture in the main pipeline is monitored and compared to a pressure of the sample in a sampling probe in which the sample is collected from the main multiphase mixture. For isokinetic sampling the pressure differential between the two pressures is minimized to a value close to zero. Under isokinetic sampling conditions, the velocity of the sample in the sampling probe opening should be approximately the same as the velocity of the multiphase mixture in the pipeline upstream of the sampling probe opening. A valve or the like may be used to maintain a differential pressure between the sample and the multiphase mixture at the sampling location at a null value. And a processor or the like may monitor the pressure differential and repeatedly/constantly adjust the valve or the like to maintain the isokinetic sampling conditions.

In step 160, the sample is flowed away from the sampling location in a slug-type flow. The slug-type flow provides that the different phases of the multiphase mixture in the sampling line flow as slugs of a single phase fluid. In certain aspects, emulsions of oil and water or the like may form causing a certain amount of liquid phase mixing. Slug-type flow in the sampling line from the sampling probe may be attained in certain embodiments of the present invention by using a small internal diameter sampling conduit. Merely by way of example, in certain aspects, a sampling conduit with an internal diameter of less than 10 mm may be used through which to flow the sample.

In step 170, a phase of the slug-type flow may be determined at one or more locations.

In certain aspects a phase detector, such as an optical phase detector, a microwave phase detector, a radiation phase detector, an electrical phase detector and/or the like may be used to determine the presence of a single phase of the multiphase mixture at a location on the sampling conduit. Because the sample is essentially separated into individual phases, detection of the presence of a phase at a certain location may be fairly simply performed in aspects of the present invention by numerous different means.

In step 180, temporal (time-continuous) measurements are made with regard to the phases flowing past the phase detection location. From comparisons of these temporal measurements for each of the different phases detected at the phase detection location, a processor or the like may compute the fraction of each phase in the sample. In embodiments of the present invention, the phase fractions may be calculated without analysis of the fluid properties of the sample, such as density, temperature, slip factors and/or the like. Moreover, from an assumption regarding the basic phase components of the multiphase mixture, i.e. the multiphase mixture comprises essentially water, oil and gas, and from data obtained from the phase detector of amplitude readings, corrections to phase detection can be made to correct for emulsions of oil and water formed in the slug-type flow.

In step 183, the output the temporal phase detection measurements may be combined with further measurements to determine a volumetric flow rate for each phase of the multiphase sample. In other aspects, a plurality of phase detectors may be used and the temporal outputs from the two phase detectors may be cross-correlated. From this cross-correlation and the distance between the phase detectors a velocity, and hence a volumetric flow rate may be determined for one or more phases of the sample of the multiphase mixture, given the sample phase fractions measured from step 180.

In step 186, a phase property sensor may be used to determine properties of a sensed phase. In certain embodiments of the present invention, one or more phase property sensors may be used in conjunction with the phase detector to determine additional properties of a sensed phase. In certain aspects, a processor may be coupled with the phase detector and based upon the location of the phase detector and the phase property sensor may control the phase property sensor to take measurements when a specific phase is at the location of the phase property sensor. In this way, the phase property sensor may perform accurate and efficient measurements on a single selected phase of the sample of the multiphase mixture; measurements that do not require interpretation and/or interpolation because the phase property sensor is taking measurements of an unknown and/or a mixed phase of a sample.

Merely by way of example, in certain aspects a densitometer, such as a nuclear-type densitometer, a Coriolis-type densitometer and/or the like may be used to determine a density of a sensed phase. In other aspects, a phase property sensor capable of determining a resistivity of a phase, a permittivity of a phase, presence of a particular element in a phase, chemical composition of a phase, salinity of a phase, salt species of a phase, pH of a phase, viscosity of a phase, $CO_2$ concentration of a phase, $H_2S$ concentration of a phase, corrosion inhibitor and/or hydrate inhibitor (e.g. methanol) concentration of a phase and/or the like may be used to determine properties of a specific phase of the sample flow. Merely by way of example, in certain aspects, volumetric flow for a phase of the slug type flow determined from temporal measurements from the phase detector may be combined with density measurements or the like to determine a mass flow rate of a single phase of the sample. In other examples, salinity measurements, conductivity measurements, spectral measurements, permittivity measurements and/or the like regarding single phases of the sample flow may be combined with phase fraction measurements to determine mass flow rates, salt content, presence of certain gas or liquid elements in a phase and/or the like for one or more phases of the sample flow.

In step 189, a sample of one or more phases of the sample flow may be selectively withdrawn. In certain aspects, a processor or the like may receive input data from the phase detector and may process the input data, the position of a sampling device relative to the phase detector, a flow rate of the sample and/or the like to control the sampling device to withdraw one or more phases from the sample. The sampling device may comprise a pump, a piston, at least a sampling probe and/or the like to provide for extraction of an amount of one or more phases of the sample. The extracted amount of the phase may be analyzed by downhole and/or subsea equipment or removed to the surface for analysis.

In step 190, flow properties of the multiphase mixture in the pipeline may be determined. In an embodiment of the present invention, a ratio between a cross-sectional area of the sampling conduit and a cross-sectional area of the pipeline at a cross-section of the pipeline from which the sample is obtained from the pipeline may be used to process total volume flow rates of the multiphase mixture and/or each phase of the multiphase mixture in the pipeline.

In step 190, the data collected from the phase detector, the phase property sensor and/or the collected sample may be combined and processed to determine properties of the sample and the component phases of the sample. As observed above, in an embodiment of the present invention, by maintaining the sample as a slug-type flow, detecting a phase and then sensing properties of a detected phase and/or sampling a detected phase, more accurate data regarding the phases may be obtained from simple sensors with less data analysis requirements.

In the foregoing description, for the purposes of illustration, various methods and/or procedures were described in a particular order. It should be appreciated that in alternate embodiments, the methods and/or procedures may be performed in an order different than that described.

Hence, while detailed descriptions of one or more embodiments of the invention have been given above, various alternatives, modifications, and equivalents will be apparent to those skilled in the art without varying from the spirit of the invention.

Moreover, except where clearly inappropriate or otherwise expressly noted, it should be assumed that the features, devices and/or components of different embodiments can be substituted and/or combined. Thus, the above description should not be taken as limiting the scope of the invention, which is defined by the appended claims.

What is claimed is:

1. A method for spot check analysis or spot sampling of a multiphase mixture flowing in a pipeline, comprising:

using a sampling probe to collect a sample of the multiphase mixture under isokinetic conditions, wherein the multiphase mixture comprises a mixture of a liquid phase and a gas phase and the liquid phase comprises at least one of a water phase and an oil/condensate phase, and wherein the sampling probe comprises a probe opening having an internal diameter for collecting the sample of the multiphase mixture;

flowing the collected sample through a conduit, wherein the conduit is configured to provide that capillary effects dominate flow of the collected sample through the conduit, and wherein the capillary effects produce a phase separated slug flow through the conduit comprising a separated flow of the gas phase, the water phase and the oil/condensate phase in the conduit;

reducing a velocity of the flow of the sample flowing in the conduit;

detecting a presence of the gas, water or oil/condensate phases in the phase separated slug flow at a first phase detection location along the conduit using a first phase detector;

detecting a presence of one of the of the gas, water or oil/condensate phases in the phase separated slug flow at a second phase detection location along the conduit using a second phase detector; and cross-correlating the detected phases at the first and the second locations to determine a phase fraction of the gas, water or oil/condensate phases in the multiphase mixture using a processor.

2. The method of claim 1, further comprising:

conditioning the multiphase mixture flowing in the pipeline upstream of a sampling location, wherein the sampling location is disposed at a cross-section of the pipeline from which the sample is retrieved.

3. The method of claim 1, wherein the step of cross-correlating the detected phases at the first and the second locations comprises using temporal measurements of a time taken for a slug of one of the gas, water or oil/condensate phases to flow a known distance L between the first and the second locations and the distance L to determine a velocity of the sample in the conduit.

4. The method of claim 1, further comprising:

using the phase fraction for the gas, water or oil/condensate phases to determine one of a water-liquid ratio, a gas-oil/condensate ratio and a gas-liquid ratio.

5. The method of claim 1, further comprising:

outputting data from the first phase detection location regarding a presence of a single phase of the multiphase mixture at the detection location; and using the output data to selectively sample the single phase.

6. The method of claim 3, further comprising:

using the phase fraction, the velocity and a cross-sectional area of the conduit to determine one of a volume flow rate of the collected sample, a liquid volume flow rate of the liquid phase, a gas volume flow rate of the gas phase, a water volume flow rate of the water phase and an oil volume flow rate of the oil/condensate phase.

7. The method of claim 6, further comprising:

using one of the volume flow rate, the liquid volume flow rate, the gas volume flow rate, the water volume flow rate and the oil volume flow rate and a ratio between the conduit cross-sectional area and a cross-sectional area of the pipeline to determine one of a total volume flow rate of the multiphase mixture in the pipeline, a total liquid volume flow rate of the liquid phase in the pipeline, a total gas volume flow rate of the gas phase in the pipeline, a total water volume flow rate of the water phase in the pipeline and a total oil volume flow rate of the oil phase in the pipeline, wherein the cross-sectional area of the pipeline is the cross-section area of the pipeline at a location in the pipeline from which the sample was collected.

8. A system for spot check analysis or spot sampling of a multiphase mixture flowing in a pipeline, comprising:
a sampling probe for retrieving a sample of the multiphase mixture from a sampling location in the pipeline, wherein the sampling probe comprises a sampling probe opening having an internal diameter;
a differential pressure sensor configured to determine a differential pressure between a pipeline pressure of the multiphase mixture at the sampling location and a probe pressure of the sample in the probe;
one or more valves coupled with the sampling probe;
a first processor coupled with the differential pressure sensor and the one or more valves and configured to control the one or more valves to provide that the sample is obtained under isokinetic conditions by nulling the differential pressure;
a conduit coupled with the sampling probe having an internal diameter and being configured to provide that capillary effects dominate flow of the sample in the conduit, wherein the capillary effects prevent a stratified flow of the sample in the conduit and produce a phase separated slug flow of the sample in the conduit, and wherein a maximum internal diameter of the conduit is larger than then internal diameter of the sampling probe to provide that velocity of the flow of the sample in the conduit is reduced with respect to velocity of the flow of the sample in the conduit;
a first phase detector to detect a phase of the sample at a first location along the conduit;
a second phase detector to detect a phase of the sample at a first location along the conduit, wherein the first and the second phase detectors are separated by a known distance L along the conduit; and
a second processor configured to process a volume of at least one of the gas, water or oil/condensate phases flowing in the multiphase mixture and a phase fraction of the gas, water or oil/condensate phases in the multiphase mixture from outputs from the first and the second phase detectors.

9. The system of claim 8, further comprising:
a flow conditioner coupled with the pipeline upstream of the sampling location and configured to condition the multiphase mixture.

10. The system of claim 8, further comprising:
a sampling device coupled with the conduit and disposed downstream of the first phase detector.

11. The system of claim 10, further comprising:
a sampling processor coupled with the first phase detector and the sampling device and configured to control the sampling device to collect a phase sample of the detected phase.

12. The system of claim 8, wherein the second processor uses cross-correlation of outputs from the first and the second phase detectors to process temporal measurements of a time taken for a phase detected at the first phase detector to flow to and be detected by the second phase detector.

13. The system of claim 10, further comprising:
a flow meter coupled with the sampling probe or the conduit and configured to determine a flow rate of the sample.

14. The system of claim 8, wherein the first phase detector comprises one of an optical sensor, an electrical sensor, a microwave sensor, a millimeter-wave sensor, a nuclear sensor, and an acoustic sensor.

15. The system of claim 8, wherein the conduit has an internal diameter of less than 10 mm.

16. The method of claim 1, wherein reducing a velocity of the flow of the sample flowing in the conduit comprises providing that an internal diameter of the conduit is larger than the internal diameter of the probe opening.

17. The system of claim 8, wherein the sampling probe has an internal diameter of less than 2 mm.

* * * * *